United States Patent [19]
Kutyavin et al.

[11] Patent Number: 5,659,022
[45] Date of Patent: Aug. 19, 1997

[54] OLIGONUCLEOTIDE-CYCLOPROPAPYRROLOINDOLE CONJUGATES AS SEQUENCE SPECIFIC HYBRIDIZATION AND CROSSLINKING AGENTS FOR NUCLEIC ACIDS

[75] Inventors: Igor V. Kutyavin; Eugeny A. Lukhtanov; Howard B. Gamper; Rich B. Meyer, Jr.; Alexander Gall, all of Bothell, Wash.

[73] Assignee: Epoch Pharmaceuticals, Inc., Bothell, Wash.

[21] Appl. No.: 583,435

[22] Filed: Jan. 5, 1996

[51] Int. Cl.$^6$ .............. C07H 19/00; C07H 21/02; C07H 21/04; A01N 43/04
[52] U.S. Cl. .......... 536/22.1; 536/23.1; 536/24.3
[58] Field of Search ............... 536/24.3, 22.1, 536/23.1; 514/397, 44

[56] References Cited

U.S. PATENT DOCUMENTS

| | | | |
|---|---|---|---|
| 4,400,518 | 8/1983 | Wierenga | 548/433 |
| 4,413,132 | 11/1983 | Wierenga | 548/491 |
| 4,423,229 | 12/1983 | Wierenga | 548/421 |
| 4,424,365 | 1/1984 | Wierenga | 548/421 |
| 4,496,492 | 1/1985 | Wierenga | 260/456 |
| 4,912,227 | 3/1990 | Kelly et al. | 548/421 |
| 4,978,757 | 12/1990 | Kelly et al. | 548/421 |
| 5,470,967 | 11/1995 | Huie et al. | 536/24.3 |
| 5,502,068 | 3/1996 | Lown et al. | 514/397 |

FOREIGN PATENT DOCUMENTS

| | | | |
|---|---|---|---|
| 93/03736 | 3/1993 | WIPO | A61K 31/70 |
| 94/17092 | 4/1994 | WIPO . | |

OTHER PUBLICATIONS

Lukhtanov et al. "Oligodeoxyribonucleotides with Conjugated Dihydropyrroloindole Olygopeptides: Preparation and Hybridization Properties", Bioconjugate Chem., 1995, vol. 6, pp. 418–426.
Webb, T.R. and Matteucci, M.D. (1986) *J. Am. Chem. Soc.*, 108, 2764–2765.
Webb, T.R. and Matteucci, M.D. (1986) *Nucleic Acids Res.*, 14, 7661–7674.
Shaw, J.-P, et al. (1991) *J. Am. Chem. Soc.*, 113, 7765–7766.
Li, T., Zeng, Q. and Rokita, S.E. (1994) *Bioconjugate Chem.*, 5, 497–500.
Knoree, D.G. and Vlassov. V.V. (1985) *Prog. Nucleic Acids Res. Mol. Biol.* 32, 291–320.
Kutyavin, I.V., et al. (1993) *J. Am. Chem. Soc.*, 115, 9303–9304.
Podyminogin, M.A., et al. (1995) *Biochemistry*, in press.
Tabone, J.C., et al. (1994) *Biochemistry*, 33, 375–383.
Povsic, T.J. and Dervan, P.B. (1990) *J. Am. Chem. Soc.*, 112, 9428–9430.
Vlassov, V.V., et al (1983) *FIBS Lets.*, 162, 286–289.
Gruff, AWES and Orgel, L.E. (1991) *Nucleic Acids Res.*, 19, 6849–6854.
Summerton, J. and Bartlett, P.A. (1978) *J. Mol. Biol.*, 122, 145–162.
Iverson, B.L. and Dervan, P.B. (1987) *J. Am. Chem. Soc.*, 109, 1241–1243.
Li, T. and Rokita, S.E. (1991) *J. Am. Chem. Soc.*, 113, 7771–7773.
Gamper, H.B., et al. (1987) *J. Mol. Biol.*, 197, 349–362.
Takasugi, M. et al. (1991) *Proc. Natl. Aced. Sci. USA*, 88, 5602–5606.
Reynold, V.L., et al. *J. Antibiotics (Tokyo)*, 39, 319–334 1986.
Boger, D.L. and Johnson, D.S. (1995) *Proc. Natl. Aced. Sci. USA*, 92, 3642–3649.
Hurley, L.H., et al. (1984) *Science*, 226, 843–844.
Warpehoski, M.A., et al. (1988) *J. Med. Chem.*, 31, 590–603.
Warpehoski, M.A. and Hurley, L.H. (1988) *Chem. Res. Toxicol.*, 1, 315–333.
Lin, C.H., et al. (1991) *Biochemistry*, 24, 3597–3602.
Reynolds, V.L., et al. (1985) *Biochemistry*, 24, 6228–6237.
Hurley, L.H., et al. (1990) *J. Am. Chem. Soc.*, 112, 4633–4649.
Boger, D.L., et al. (1994) *Bioorg. Med. Chem.*, 2, 115–135.
Kelly, R.C., et al. (1987) *J. Am. Chem. Soc.*, 109, 6837–6838.
Sugiyama, H., et al. (1994) *Chem. Res. Toxicol.*, 7, 673–683.
Maxam, A.M. and Gilbert, W. (1977) *Proc. Natl. Aced. Sci. USA*, 74, 560–564.
Baker, B.R. (1967) "Design of active–site directed irreversible enzyme inhibitors" John Wail and Sons, N.Y., pp. 156–191.
Li, C.H., et al. (1991) *Chem. Res. Toxicol.*, 4, 21–26.
Perrin, D.M., et al. (1994) *Biochemistry*, 33, 3848–3854.
Helene, C. (1991) *Anti–Cancer Drug Design*, 6, 569–584.

*Primary Examiner*—Ardin H. Marschel
*Assistant Examiner*—Jezia Riley
*Attorney, Agent, or Firm*—Klein & Szekeres LLP

[57] ABSTRACT

Covalently linked conjugates of oligonucleotides (ODNs) with a cyclopropapyrroloindole moiety or an analog thereof, selectively and efficiently alkylate and crosslink with nucleic acid sequences that are complementary to the base sequence of the ODN.

25 Claims, No Drawings

OLIGONUCLEOTIDE-CYCLOPROPAPYRROLOINDOLE CONJUGATES AS SEQUENCE SPECIFIC HYBRIDIZATION AND CROSSLINKING AGENTS FOR NUCLEIC ACIDS

BACKGROUND OF THE INVENTION

1. Field of the Invention

The present invention is directed to covalently linked oligonucleotide-cyclopropapyrroloindole conjugates which selectively hybridize with a target nucleic acid (or fragment thereof) of complementary nucleotide sequence, and which after hybridization efficiently cross-link with appropriately positioned adenine bases in the target sequence.

2. Brief Description of the Prior Art

The concept of using oligodeoxyribonucleotides and oligoribonucleotides (collectively ODNs) which sequence specifically bind to a target nucleic acid (or portion thereof) for therapeutic, diagnostic and analytical (sequence determination/gene mapping) purposes is old in the art. The use of ODNs having one or more covalently bonded cross-linking agents, to sequence specifically hybridize with a complementary target nucleic acid (or portion thereof) and therafter cross-link to the single or double stranded target, is also known in the art. Cross-linking may occur as a result of irradiation of the hybrid, for example when a psoralen moiety serves as the cross-linking agent. Published PCT applications WO 93/03736 and WO 94/17092 (assigned to the same assignee as the present application) describe oligonucleotides which include one or more covalently linked electrophilic cross linking agents, and which bind to a complementary sequence of nucleic acid (or portion thereof) followed by cross-linking (alkylation) of a base in the target sequence. The latter concept is related to the pioneering work of B. R. Baker, "Design of Active-Site-Directed Irreversible Enzyme Inhibitors," Wiley, N.Y., (1967), who used what was termed "active-site-directed enzyme inhibitors" in chemotherapeutic applications.

Important criteria for utilizing ODN-crosslinker conjugates for chemotherapeutic applications include selectivity of the ODN to reversibly bind only to the desired target sequence of nucleic acid, and effectiveness of the cross-linking reaction in terms of velocity and specificity of the reaction with the nucleophilic group in the target. In other words, it is desirable for the electrophilic group to be substantially unreactive under the conditions of the expected use of the ODN-crosslinker conjugate with nucleophiles in the reaction medium (including the cell where the therapeutic agent is expected to act) and to undergo the cross-linking reaction relatively rapidly, but only after the hybridization of the ODN portion of the conjugate to the target sequence has already occurred. Similar criteria apply to the use of ODN-electrophilic cross-linker conjugates for diagnostic and analytical applications.

Whereas, certain ODN-cross-linker conjugates known in the art before the present invention justify reasonable expectations of utility in diagnostic, analytical and chemotherapeutic applications, many suffer from shortcomings in terms of the criteria discussed above. For these and other reasons, there is definite room in the art for improvement in the nature of ODN-crosslinker conjugates for therepeutic, diagnostic and analytical use. The present invention provides such improvement.

Another aspect of the pertinent background of the present invention relates to the antitumor antibiotic dextrorotatory (+) CC-1065, the structure of which is shown in Formula 1.

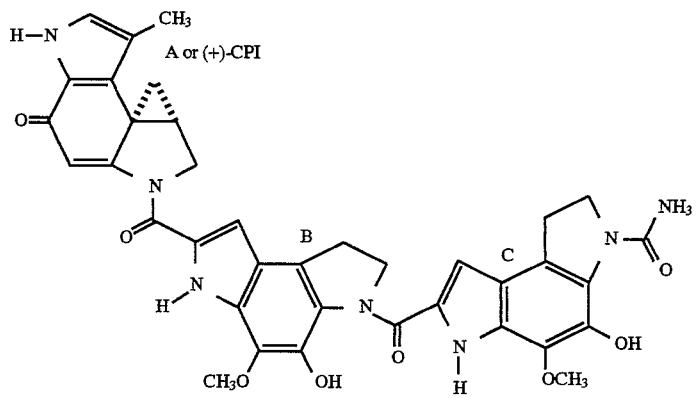

Formula 1 (+) CC-1065

As it can be seen, this antibiotic is composed of three repeating 1,2-dihydro-3H-pyrrolo[3,2-3-e]indole subunits. One of the subunits (designated as subunit "A" in Formula 1) contains an electrophilic cyclopropyl moiety. The antibiotic is very stable in neutral aqueous solution. However, it binds strongly in the minor groove of A-T rich double stranded DNA and alkylates the DNA with resultant opening of the cyclopropyl ring. Specifically, the A subunit of the natural dextrorotatory (+) enantiomer of the antibiotic binds in the minor groove of A-T rich DNA, such that this subunit is directed to an appropriately positioned adenine base, and efficiently alkylates the adenine moiety in the manner shown in Reaction Scheme 1.

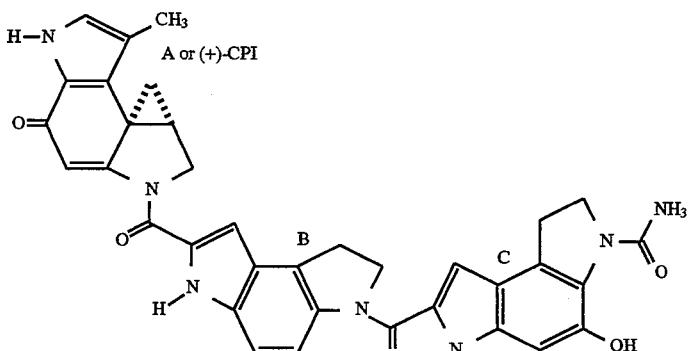

(+)-CC-1065

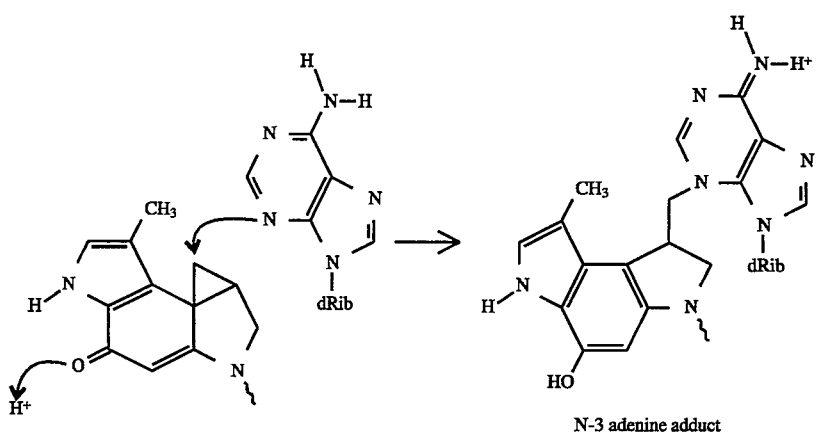

N-3 adenine adduct

Reaction Scheme 1

The (−) (levorotatory) enantiomer of the antibiotic CC-1065 binds to DNA with opposite polarity to the above-mentioned sequences in DNA. It alkylates an adenine moiety therein with approximately the same efficiency as the natural (+) enantiomer.

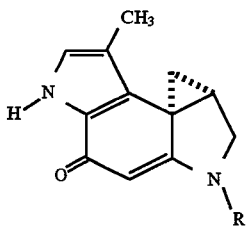

Formula 2

On the other hand, the dextrorotatory (+) cyclopropapyrroloindole subunit [(+) CPI], shown in Formula 2, of the antibiotic acting as a separate chemical entity (R═H)) is known to alkylate DNA much less efficiently than the whole antibiotic. This is presumably due to the low binding affinity of (+) CPI for A-T rich double stranded DNA. The levorotatory (−) enantiomer of CPI has a reversed binding orientation to A-T rich double stranded DNA, and alkylates DNA 10 to 100 times more slowly than the (+) CPI enantiomer. As it will be seen below, the present invention, by covalently linking the CPI moiety with an ODN, significantly raises the efficiency of the alkylation reaction between a complementary strand of nucleic acid and the ODN-CPI conjugate.

The following references describe or relate to the above described features and reactions of the antibiotic CC-1065 and its CPI subunit:

Reynolds et al. (1986) J. Antibiotics (Tokyo), 39, 319–334;

Boger et al. (1995) Proc. Natl. Acad. Sci. USA, 92, 3642–3649;

Hurley et al. (1984) Science, 226, 843–844;

Warpehoski et al. (1988) J. Med. Chem., 31, 590–603;

Warpehoski et al. (1988) Chem. Res. Toxicol., 1, 315–333;

Lin et al. (1991) Biochemistry, 30, 3597–3602;

Reynolds et al. (1985) Biochemistry, 24, 6628–6237;

Hurley et al. (1990) J. Am. Chem. Soc., 112, 4633–4649.

U.S. Pat. Nos. 4,400,518; 4,413,132; 4,423,229; 4,424,365; 4,496,492; 4,912,227; and 4,978,757 describe or relate to analogs of the antibiotic CC-1065, more particularly to analogs and derivatives of the CPI subunit of this antibiotic. These analogs are said to be useful primarily as bacteriostatic or bacteriocidal agents.

SUMMARY OF THE INVENTION

The present invention comprises covalently bonded ODN-CPI or ODN-CPI-analog conjugates which reversibly bind with their ODN portion to a target sequence of nucleic acid having a complementary or substantially complementary base sequence to the ODN. The CPI or CPI analog moiety of the ODN is located in the minor groove of the complex formed between the target sequence and the ODN-CPI conjugate, and alkylates appropriately positioned adenine bases therein, thereby cross-linking the ODN-CPI or ODN-CPI-analog conjugate with the target sequence. The ODN-CPI or ODN-CPI-analog conjugates are primarily used for complexing with and alkylating single stranded DNA, however complexing and subsequent alkylation with double stranded nucleic acid through triplex and D loop formation, especially in the presence of recombinase enzyme, is also possible. The ODN-CPI or ODN-CPI-analog conjugates can be used for diagnostic and analytical purposes, such as locating a predetermined target sequence in nucleic acids, and for therapeutic uses such as inhibiting single stranded viral DNA replication (e.g. hepatitis B virus), or as gene selective inhibitors of transcription initiation (e.g. by binding to an open promoter complex).

A general formula of the ODN-CPI conjugate of the present invention is shown below as Formula 3. In this regard it is noted that henceforth in this specification and claims the term "ODN-CPI conjugate" includes covalently bonded conjugates of ODNs with such analogs or derivatives of the CPI moiety which are encompassed in Formula 3. Thus, the term "ODN-CPI conjugate" is not limited to ODNs covalently linked with the CPI moiety as that moiety is specifically shown in Formula 2.

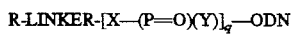

Formula 3 where q is an integer selected from 0 or 1;

the X—(P=O)(Y)— group is at the 3' or 5' end or at both ends of the ODN;

X is O or S;

Y is O⁻, S⁻ or $CH_3$;

ODN is an oligonucleotide of approximately 3 to 500 nucleotide units, wherein the sugar moiety attached to the heterocyclic bases of the nucleotides is independently selected from β 2-deoxyribofuranose, and β-2-OR'-ribofuranose where R' is $C_{1-5}$-alkyl or $C_{2-5}$-alkenyl, the heterocyclic bases may optionally include bases other than uracil, thymine, cytosine, adenine and guanine, the internucleotide linkages may optionally and independently include phosphorothioate and methylphosphonate linkages, and the ODN may optionally include an intercalator group, reporter group, lipophilic group or a minor groove binder covalently attached to the ODN;

the LINKER is a divalent moiety forming a covalent linkage between the R and (X—(P=O)(Y))$_q$ groups, of approximately 2 to 30 atoms length, and R is a group selected from the Formulas 4 and 5

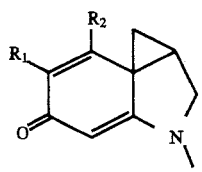

Formula 4

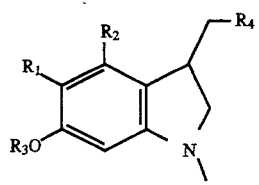

Formula 5 where $R_1$ and $R_2$ independently are H, alkyl of 1 to 6 carbons, alkoxy of 1 to 6 carbons, amino, alkylamino or dialkylamino where the alkyl group has 1 to 6 carbons, phenyl, ($C_{1-6}$alkyl)phenyl, heterocyclic consisting of a 5 to 7 membered ring and including 1 to 3 heteroatoms independently selected from the group consisting of O, N and S, ($C_{1-6}$alkyl)heterocyclic, or the $R_1$ and $R_2$ groups jointly form a carbocyclic ring of 5 to 7 atoms or a ($C_{1-6}$alkyl)carbocyclic ring of 5 to 7 atoms, a heterocyclic or a ($C_{1-6}$alkyl)heterocyclic ring where heterocyclic is defined as above, with the proviso that $R_1$ and $R_2$ are not both selected from the group consisting of phenyl, ($C_{1-6}$alkyl)phenyl, heterocyclic and ($C_{1-6}$alkyl)heterocyclic;

$R_3$ is H or a group cleavable under physiological conditions;

$R_4$ is a leaving group, with the further proviso that when q is 0 then the LINKER group is attached to the 5 position of a uracil or to the 8 position of a purine base of a 5' or 3' terminal nucleotide of the ODN.

DETAILED DESCRIPTION OF THE INVENTION

General Embodiments

A prominent feature of the present invention is that the cyclopropapyrroloindole (CPI) moiety (designated "A" in Formula 1) or an analog thereof is covalently linked to either the 3' or 5' terminus of an oligonucleotide (ODN) that has a complementary or substantially complementary sequence to a target in nucleic acid. In accordance with the invention the ODN binds to the target nucleic acid by conventional Watson Crick hydrogen bonding, and the CPI moiety (or analog thereof) is disposed in the minor groove of the resulting complex. The CPI moiety (or its analog) efficiently and relatively rapidly alkylates an adenine residue in the target sequence, provided such residue is available in an appropriate position in the target. By way of example, an adenine residue is in appropriate position in the target when the target includes 5'-ATATA* and 5'-AAAAA* sequences, where the * symbol indicates the adenine residue that becomes cross-linked with the CPI or analogous alkylating residue. Between the two above-shown exemplary sequences the 5'-AAAAA* sequence has higher affinity for alkylation by the CPI or analogous moiety than the 5'-ATATA* sequence. Alkylation of an adenine moiety in other A and T rich sequences is also possible. Moreover, whereas the primary application of the ODN-CPI conjugates of the present invention is for complexing with and alkylating single stranded DNA, complexing with double stranded nucleic acid through triplex and D loop formation is also within the contemplated use of the ODN-CPI conjugates of the present invention.

Experiments conducted in connection with the present invention have shown that ODN-CPI conjugates of the present invention are substantially stable at neutral pH (pH=7.2). The stability of the conjugate, and specifically of the cylopropane ring in the CPI (or analogous) moiety can be readily monitored by u.v. spectroscopy because opening of the cyclopropane ring and simultaneous transformation of the quinone structure into a hydroquinone structure (see Reaction Scheme 1) results in loss of absorbence between 300 and 400 nanometer. In the experiments monitored by u.v. spectroscopy in the above-summarized manner no detectable reaction of the cyclopropane ring was observed when a preferred embodiment of the ODN-CPI conjugate of the invention was incubated at pH 7.2 for 3 days. Even in the presence of 10 mM gluthathione the ODN-CPI conjugate failed to undergo detectable reaction at room temperature, and at 37° C. had a half-life of 36 hours ($t_{1/2}=36$ hours). In contrast, when the same preferred embodiment of the ODN-CPI conjugate was incubated with a complementary single stranded DNA at 37° C. the half life of the cyclopropane ring was only 2 minutes ($t_{1/2}=2$ min).

The general structure of the CPI analog which is covalently linked to either the 3' or 5' terminus (or both) of an oligonucleotide (ODN) that is complementary or substantially complementary to a target sequence is provided above in Formulas 4 and 5. With reference to these two formulas, ODN-CPI conjugates are presently preferred in accordance with the present invention where the $R_3$ group is H or a group that cleaves under the physiological conditions of using the conjugate. In this regard the $R_3$ may be an acyl group of an alkanoic acid of 1 to 6 carbons (such as acetyl) or phosphoryl group or other group which forms a readily cleavable ester, as well a water labile trimethylsilyl or like trialkylsilyl group.

With regard to the $R_1$ and $R_2$ groups in Formulas 4 and 5, compounds are preferred in accordance with the present invention where $R_1$ and $R_2$ joint iy form a carbocyclic or heterocyclic ring, even more preferably a pyrrol ring, and still more preferably a lower alkyl (such as methyl) substituted pyrrol ring, as is shown in the corresponding moiety in Formula 1 and Formula 2.

The $R_4$ group of Formula 5 is a leaving group, such that the structure shown in Formula 5 is activated under physiological condition to form the cyclopropyl ring, or to act as an alkylating agent per se, to provide, after cross-linking, N-alkylated adenines in the target sequence. Examples for the $R_4$ leaving group are Cl, Br, I, $OSO_2R''$ where R'' is ($C_{1-6}$)alkyl, phenyl, tolyl, bromophenyl, nitrophenyl, and trifluoromethyl, with the chloro group being presently preferred.

Referring still to Formulas 4 and 5, it is apparent that the CPI or CPI analog moiety incorporated into the ODN-CPI conjugates of the present invention exists in enantiomeric forms, similar to the (+) and (−) forms of the naturally occurring CC-1065 antibiotic. Both enantiomers of the preferred embodiment of the ODN-CPI conjugates do not cross-link with the target sequence with equal efficiency; the conjugate incorporating the (+) enantiomer was found to be more efficient than the conjugate having the (−) enantiomer. Those skilled in the art will readily understand however, that the dextrorotatory or levorotatory nature of a compound is determined by the entirety of its structure, and therefore it is not entirely predictable whether in any given structure within the scope of Formulas 4 and 5 the optically dextrorotatory or levorotatory enantiomer will be more reactive in the cross-linking reaction between the ODN-CPI conjugate and the complementary target nucleic acid. This can neverthless be determined without undue experimentation. In any event, even if one of the enantiomers of a compound within the scope of the present invention were substantially inactive in the cross-linking reaction, the ODN-CPI conjugate incorporating the racemic mixture of the CPI analog is expected to be active. For these reasons, ODN-CPI conjugates incorporating either or both enantiomers of the CPI and analog moiety or their racemic mixture are all considered within the scope of the invention.

Broadly speaking, the oligonucleotide portion of the ODN-CPI conjugates of the present invention comprises approximately 3 to 500 nucleotide units. The nucleotide units which can be incorporated into the ODN-CPI conjugates in accordance with the present invention include the major heterocyclic bases naturally found in nucleic acids (uracil, cytosine, thymine, adenine and guanine) as well as naturally occurring and synthetic modifications and analogs of these bases such as hypoxanthine, 2-aminoadenine, 2-thiouracil, 2-thiothymine, 5-$N^4$ ethenocytosine, 4-aminopyrazolo[3,4-d]pyrimidine and 6-amino-4-hydroxypyrazolo[3,4-d]pyrimidine.

The "sugar" or glycoside portion of the ODN-CPI conjugates of the present invention may comprise 2-deoxyribofuranose, and 2-O alkyl or 2-O-alkenylribofuranose where the alkyl group may have 1 to 5 carbons and the alkenyl group 2 to 5 carbons. The glycosydic linkage in these sugar moieties is of the β configuration and the purine bases are attached to the sugar moiety via the 9-position, the pyrimidines via the 1-position and the pyrazolopyrimidines via the 1-position. Presently, oligodeoxyribonucleotides are preferred in accordance with the present invention, therefore the preferred sugar is 2-deoxyribose. The nucleotide units of the ODN-CPI conjugates are interconnected by a "phosphate" backbone, as is well known in the art. The ODNs of the ODN-CPI conjugates of the present invention may include, in addition to the "natural" phosphodiester linkages, one or more phosphorothioates and methylphosphonates, or may have entirely phosphorothioate or methylphosphonate backbones.

The ODNs of the ODN-CPI conjugates of the present invention may also have a relatively low molecular weight "tail moiety" attached to either at the 3' or 5'-end. The "tail moiety" in this particular context is to be distinguished from the CPI or CPI analog moiety, and the "tail moiety" is attached to the terminus opposite to which the CPI moiety is attached. Thus, the "tail moiety" if present at all, is attached to the end of the ODN which does not bear the CPI moiety. By way of example, a tail molecule may be a phosphate, a phosphate ester, an alkyl group, an aminoalkyl group, a lipophilic group, (such as cholesteryl or other "steroid" radical) or a reporter group.

With regard to the possible variations of the nucleotide units, the "phosphate backbone" and "tail" of the ODNs of the ODN-CPI conjugates of the present invention, the following should be kept in mind. The principal useful action of the ODN-CPI conjugates of the present invention lies in the ability of the ODN portion of the molecule to bind to a complementary sequence in single stranded DNA, and in some cases to double stranded DNA, followed by efficient cross-linking of the target by the CPI analog moiety which acts as an alkylating agent. In light of the foregoing, those skilled in the art will readily understand that the primary structural limitation of the various component parts of the ODN portion of the ODB-CPI conjugate of the present invention lies only in the ability of the ODN portion to form a reversibly bound complementary sequence to any specific target sequence, and that a large number of structural modifications, per se known in the art, are possible within these bounds. Moreover, synthetic methods for preparing the various heterocyclic bases, nucleosides, nucleotides and oligonucleotides which can form the ODN portion of the ODN-MCB conjugates of the present invention, are generally speaking well developed and known in the art. $N_4,N_4$-ethano-5-methyldeoxycytidine, its nucleoside, nucleotide and/or oligonucleotides incorporating this base can be made in accordance with the teachings of (a) Webb, T. R.; Matteucci, M. D. *Nucleic Acids Res.*, 1986, 14, 7661–7674, (b) Webb, T. R.; Matteucci, M. D. *J. Am. Chem. Soc.*, 1986, 108, 2764. 4-aminopyrazolo[3,4-d]pyrimidine, 6-amino-4-hydroxypyrazolo[3,4-d]pyrimidine, their nucleosides, nucleotides and oligonucleotides incorporating this base can be made in accordance with the teachings of Kazimierczuk et al. *J. Am. Chem. Soc.*, 1984, 106, 6379–6382.

Whereas oligonucleotide synthesis, in order to prepare an ODN of specific predetermined sequence so as to be complementary to a target sequence, can be conducted in accordance with the state of the art, a preferred method is described below. Another method is described in U.S. Pat. No. 5,419,966, the specification of which is expressly incorporated herein by reference.

Referring now to the group designated LINKER in Formula 3, this is a linking group which covalently links the CPI or analogous moiety (as defined in Formulas 4 and 5) to the ODN moiety. Preferably, the CPI or CPI analog is attached through the linking group to the phosphate or analogous terminus of the ODN, and therefore q of Formula 3 is preferably 1 (one). The group designated Y in Formula 3 is preferably O. In alternative embodiments the CPI or CPI analog moiety is attached through the linking group to the 5 position of a uracil or to the 8 position of a purine base, with the uracil or purine base being located at the 3' or 5' terminus of the ODN. In such cases g of Formula 3 is 0.

Generally speaking, the linking group is derived from a bifunctional molecule so that one functionality, such as a hydroxyl functionality, is attached for example to the phosphate on the 5' or 3' end of the ODN, and the other functionality such as a carbonyl group (CO) is attached to the ring nitrogen in the cyclopropapyrrolo group of the CPI or CPI analog. moiety. Alternatively, the linking group may be derived from an amino alcohol so that the alcohol function is linked to the 3'-phosphate or 5'-phosphate end of the ODN and the amino function is linked through a carbonyl group to the above-mentioned ring nitrogen.

Still another alternative example of a linking group includes an aminoalcohol (attached to the 3' or 5'-phosphate with an ester linkage) linked to a dicarboxylic acid with a peptide bond, which in turn is linked through its second carbonyl group to the ring nitrogen of the cyclopropapyrrolo group. Yet another alternative example of the linking group includes a —CH$_2$—S linkage to a phosphorothioate group at the 3' or 5' terminus of the ODN, where the methylene group is linked to the ring nitrogen through further peptide bonds. As a still further alternative example of the linking group, an alkylamine (such as a hexylamine) tail is attached to the 3'- or 5'-phosphate terminus of the ODN by a phosphate ester linkage, the amine function is connected with a dicarboxylic acid radical to tricyclic moiety, such as a subunit of the antibiotic CC-1650. The latter, in turn, is connected with a carbonyl group to the CPI or CPI analog moiety. The linking group may also include an "internal" ether (such as —CH$_2$OCH$_2$—) or sulfide (such as —CH$_2$SCH$_2$—) linkage.

Thus, preferred embodiments of the linking group have the formulas:

—O(CH$_2$)$_m$CO—;

—O(CH$_2$)$_m$NHCO—;

—O(CH$_2$)$_m$NHCO(CH$_2$)$_n$CO—;

—(CH$_2$)$_m$CO— when X of Formula 3 is preferably S;

—(CH$_2$)$_m$CONH(CH$_2$)$_n$CO— when X of Formula 3 is preferably S;

—(CH$_2$)$_m$CH(OH)(CH$_2$)$_n$NHCO(CH$_2$)$_p$NHCO—;

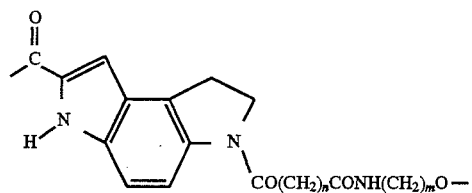

and

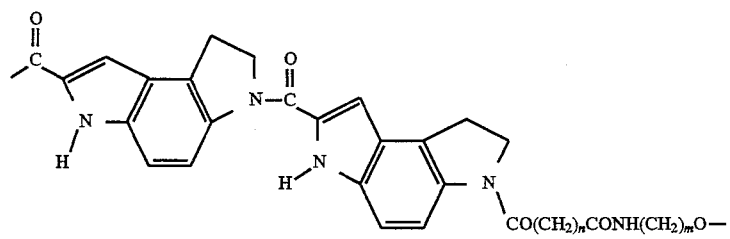

where the limitation on m, n and p is that the CPI or CPI analog moiety should not be separated by more than approximately 30 atoms from the ODN as counted in a direct line. Examples of more preferred embodiments of linking groups are shown below in formulas where the CPI or CPI analog unit is designated R, and the 3' or 5' phosphate end of the ODN is also shown:

R—CO—(CH$_2$)$_n$—CONH—(CH$_2$)$_k$—OPO(O$^-$)—ODN (n=2 or 3; k=4, 5 or 6);

R—CO—(CH$_2$)$_2$—CONH—(CH$_2$)$_2$O(CH$_2$)$_2$—O—OPO (O$^-$)—ODN;

R—CO—(CH$_2$)$_n$—NHCOCH$_2$—S—OPO (O$^-$)—ODN (n=2–5);

R—CO—CH$_2$—S—OPO(O$^-$)—ODN,

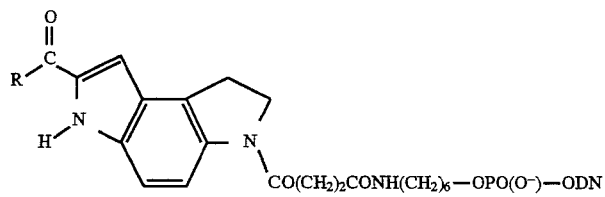

and

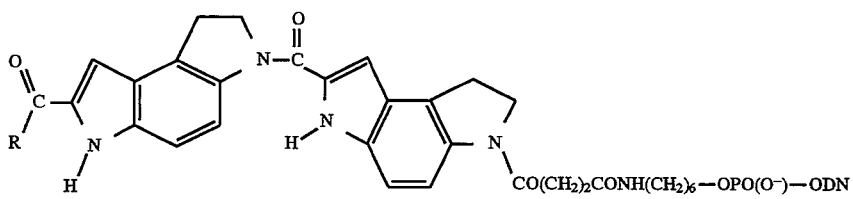

Synthesis of CPI analogs, and ODN-CPI conjugates

Reaction Scheme 2 below provides examples for the synthesis of ODN-CPI conjugates wherein the CPI moiety of the antibiotic CC-1065 is covalently linked to an 18-mer oligodeoxyribonucleotide (18-mer) through a presently preferred linking group. The sequences of the two ODNs (before they are modified and linked to the CPI moiety through a linking group) are provided below as Sequence Id. No: 1 and Sequence Id. No: 2, respectively.

Sequence Id. No: 1  3'-TTTTTTCGCCAATCGAGG-5'.
Sequence Id. No: 2  3'-GGGTACAACACGTTTTTT-5'
Sequence Id. No: 3  5'-CCCATGTTGTGCAAAAA AGCGGTTAGCTCC-3'.

Sequence Id. No: 3 provided above is the sequence of a 30-mer which contains complementary sequences to both 18 mers of Sequence Id. No: 1 and Sequence Id. No: 2. More particularly Sequence Id. No: 1 is complementary to the sequence at the 3' end of the ODN of Sequence Id. No: 3, and Sequence Id. No: 2 is complementary to the sequence at the 5' end of the ODN of Sequence Id. No: 3.

Reaction Scheme 2

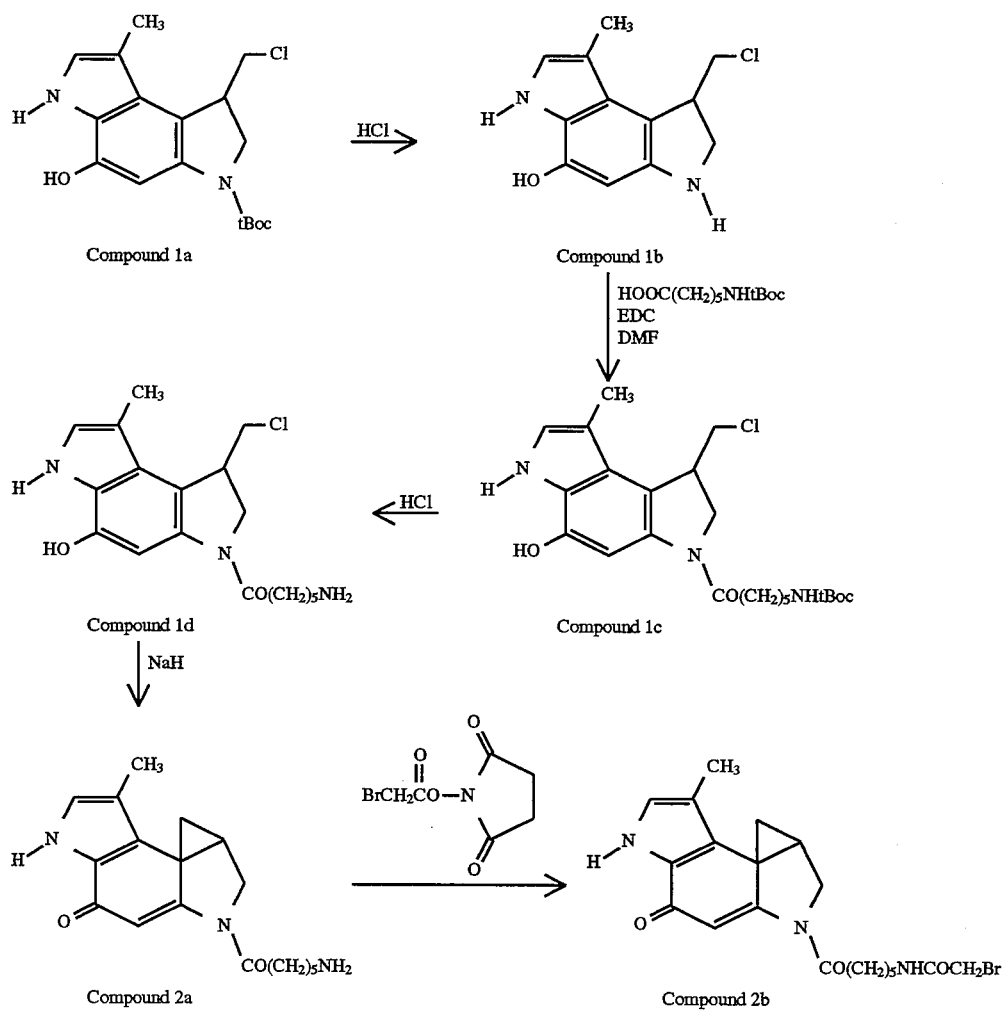

-continued
Reaction Scheme 2

Sequence Id. No: 4  +  Compound 2b

↓ aqueous DMF

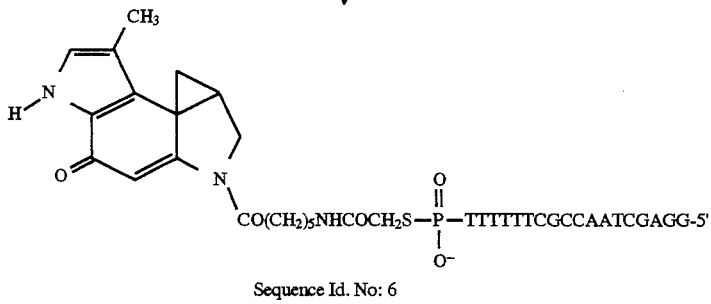

Sequence Id. No: 6

Sequence Id. No: 5  +  Compound 2b

↓ aqueous DMF

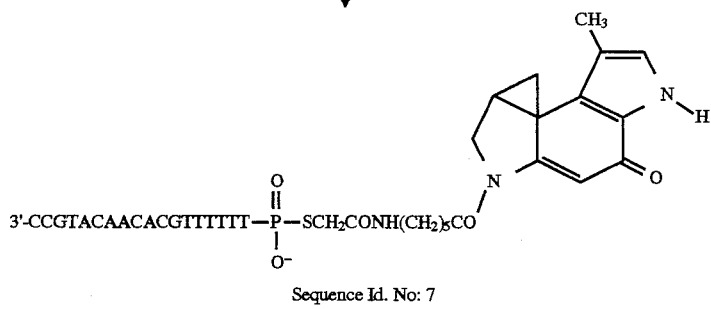

Sequence Id. No: 7

Referring now particularly to Reaction Scheme 2, racemic 1-(chloromethyl)-1,6-dihydro-5-hydroxy-8-methylbenzo[1,2-b:4,3-b']dipyrrole-3(2H)-carboxylic acid t-butyl ester (1a) is treated with acid to remove the t-butyloxycarbonyl protective group and to yield 1-(chloromethyl)-1,6-dihydro-5-hydroxy-8-methylbenzo[1,2-b:4,3-b']dipyrrole (1b). The starting material 1a is obtained and the latter reaction is conducted in accordance with the literature procedure; Hurley et al. (1990) J. Am. Chem. Soc. 112, 4633–4649, incorporated herein by reference. Compound 1b is thereafter acylated on the nitrogen of the pyrrolidene ring by treatment with t-butyloxycarbonyl protected 6-aminocaproic acid in dimethylformamide (DMF) in the presence of N(3-dimethylaminopropyl)-N'-ethylcarbodiimide (EDC) to yield the corresponding N-acylated derivative, 6-(N-tert-butyloxycarbonyl-6-aminohexanoyl)-8-chloromethyl-3,6,7,8-tetrahydro-1-methylbenzo[1,2- b:4,3-b']dipyrrol-4-ol (1c). The t-butyloxycarbonyl protecting group is removed from 1c by treatment with acid to give 6-(6-aminohexanoyl)-8-chloromethyl-3,6,7,8-tetrahy-dro-1-methylbenzo[1,2-b:4,3-b']dipyrrol-4-ol (1d). Compound 1d is reacted with strong base (NaH) to close the cyclopropyl ring, yielding 2-(6-aminohexanoyl)-1,2,8,8a-tetrahydro-7-methylcyclopropa[c]pyrrolo[3,2-e]indol-4(5H)-one (2a). Compound 2a is thereafter reacted with an active ester (N-hydroxysuccinimide ester) of bromoacetic acid to attach the bromoacetyl group to the amino group of the aminocaproic acid moiety, yielding 2-(N-bromoacetyl-6-aminohexanoyl)-1,2,8,8a-tetrahydro-7-methylcyclopropa[c]pyrrolo[3,2-e]indol-4 (5H)-one (2b). Compound 2b is a preferred example of a CPI-linking-group-combination having a reactive group (the bromoacetyl group) that enables attachment of the CPI-linking-group-combination to an ODN. As is noted above, the ODN is specifically selected and synthesized (if not otherwise available) to be complementary to a target sequence in nucleic acid. In the herein described preferred examples the ODNs linked with the CPI-linking-group-combination are the oligodeoxyribonucleotides of Sequence Id. No: 1 and of Sequence Id. No: 2 which are prepared in accordance with the state of the art.

Continuing now with the description of Reaction Scheme 2, first the ODNs of Sequence Id. No: 1 and of Sequence Id. No: 2 are sulfurized in accordance with the state of the art to give the 3' and the 5'-phosphorothioate tailed ODNs, Sequence Id No. 4 and Sequence Id. No: 5, respectively. These are shown below.

Sequence Id. No: 4  3'-HS(O⁻)PO-TTTTTTCG CCAATCGAGG-5'.

Sequence Id. No: 5  3'-GGGTACAACACGTTTTTT-PO (O⁻)SH-5'

The ODNs of Sequence Id. No: 4 and Sequence Id. No: 5 are then reacted with 2-(N-bromoacetyl-6-aminohexanoyl)-1,2,8,8a-tetrahydro-7-methylcyclopropa[c]pyrrolo[3,2-e]indol-4(5H)-one (2b) to give the respective 3' and 5' end CPI-ODN conjugates, which are depicted in Reaction Scheme 2 and have the designations Sequence Id. No: 6 and Sequence Id. No: 7, respectively. These ODNs (Sequence Id. No: 6 and Sequence Id. No: 7) include the cyclopropyl cross linking agent.

Generally speaking, the various embodiments of the CPI analogs corresponding to Formulas 4 and 5 can be prepared in accordance with the teachings of U.S. Pat. Nos. 4,400, 518; 4,413,132; 4,423,229; 4,424,365; 4,496,492; 4,912, 227; and 4,978,757, modified to such extent as necessary and as will be readily apparent to those skilled in the art of synthetic organic chemistry. The specifications of U.S. Pat. Nos. 4,400,518; 4,413,132; 4,423,229; 4,424,365; 4,496,492; 4,912,227; and 4,978,757 are expressly incorporated herein by reference. The compounds corresponding to the CPI analogs shown in Formulas 4 and 5 can, generally speaking, be incorporated in the CPI-ODN conjugates of the present invention in accordance with the steps exemplified in Reaction Scheme 2 or by such modifications thereof which are within the skill of the person practicing this art.

DNA cross-linking activity

As noted above the ODNs of Sequence Id. No: 6 and Sequence Id. No: 7 have an electrophilic group (the cyclopropyl cross-linking agent) These compounds were nevertheless found to be stable when incubated in neutral aqueous solution, and even when incubated with 10 mM gluthathione at room temperature. When incubated with the target ODN of Sequence Id. No: 3, the CPI-ODN conjugate of Sequence Id. No: 6 alkylated the target rapidly, with a half-life of the cyclopryl chromophor of 2 min at 37° C., as indicated by u. v. monitoring and PAGE electrophoretic analysis. The CPI-ODN conjugate of Sequence Id. No: 7 alkylated the same target significantly slower, but nevertheless alkylated it, as indicated by PAGE electrophoretic analysis. The PAGE electrophoretic analysis also showed that the sites of alkylation in the target ODN of Sequence Id. No: 3 were on the adenine residues of the six consecutive adenine sequence, with the second adenine (from the 3' end) in this group being the predominant site of alkylation. Significantly, when the CPI-ODN conjugates of Sequence Id. No: 6 and of Sequence Id. No: 7 were incubated with a non-complementary 30-mer of Sequence Id. No: 8, no alkylation reaction was observed.

Sequence Id. No: 8 5'-TCGTTGTCAGAAGTAAGTT GGGCCGCAGTGT

In light of the foregoing, the cross-linking reaction of the CPI-ODN conjugates of the present invention is specific to cross-linking with a nucleic acid sequence to which the ODN moiety of the conjugate is complementary. The cross-linking reaction is also specific or highly selective in the sense that non-specific alkylation of nucleophiles in the medium does not occur or is significantly slower than the ODN-site directed cross-linking. Still further, attachment of the CPI moiety to the 3' end of the ODN is preferable over attachment to the 5' end, although both are within the scope of the invention.

SPECIFIC EMBODIMENTS—EXPERIMENTAL SECTION

Materials and Methods

All air and water sensitive reactions were carried out under argon. Anhydrous solvents were obtained from Aldrich (Milwaukee, Wis.). Flash chromatography was performed on 230–400 mesh silica gel. UV-visible absorption spectra were recorded on a Lambda 2 (Perkin Elmer) spectrophotometer with a PTP-6 temperature controller. $^1$HNMR spectra were run at 20° C. on a Varian 300 spectrometer; and chemical shifts are reported in ppm downfield from $Me_4Si$. Racemic compound 1-(chloro methyl)-1,6-dihydro-5-hydroxy-8-methylbenzo[1,2-b:4,3-b']dipyrrole-3(2H)-carboxylic acid t-butyl ester 1a was prepared as previously described (Warpehoski et al., (1988) J. Med. Chem., 31, 590–603; Hurley et al. (1990) J. Am. Chem. Soc., 112, 4633–4649, and Kelly et al., J. Am. Chem. Soc., 109 6837–6838 (1987).

6-(N-tert-butyloxycarbonyl-6-aminohexanoyl)-8-chloromethyl-3,6,7,8-tetrahydro-1-methylbenzo[1,2-b:4,3-b']dipyrrol-4-ol (Compound 1c)

Racemic 1-chloromethyl derivative 1a (0.22 g, 0.65 mmol) was converted into 1-(chloromethyl)-1, 6-dihydro-5-hydroxy-8-methylbenzo[1,2-b:4,3-b']dipyrrole (1b) by treatment with HCl in ethyl acetate according to the literature procedure (see Hurley et al. (1990) J. Am. Chem. Soc., 112, 4633–4649). The hydrochloride 1b was dissolved in 10 mL of anhydrous DMF to which Boc-N-aminocaproic acid (0.31 g, 1.3 mmol) and $\underline{N}$ (3-dimethylaminopropyl)-$\underline{N}$'-ethylcarbodiimide (EDC) (0.77 g, 4 mmol) were added. After stirring for 3 hours, the reaction mixture was concentrated in vacuo to an oil and triturated with water (25 mL). The resulting solid was centrifuged, washed with water, centrifuged again, and dried in vacuo. The resulting crude material was purified by flash chromatography in dichloromethanemethanol (9:1) to give the title compound (1c) as an off-white solid (0.195 g, 67%):

$^1$H NMR (CDCl$_3$) δ10.27 (s, 1H), 9.40 (s, 1H), 8.20 (s, 1H), 7.00 (s, 1H), 4.30 (br s, 1H), 4.4–3.8 (m, 4H), 3.4–3.1 (m, 3H), 2.7–2.45 (m, 2H), 2.42 (s, 3H), 2.0–1.7 (m, 2H), 1.7–1.3 (m, 13H, partially overlapping with H$_2$O, 1.48 ppm—$^t$BOC singlet).

2-(N-bromoacetyl-6-aminohexanoyl)-1,2,8,8a-tetrahydro-7-methylcyclopropa[c]pyrrolo[3,2-e]indol-4(5H)-one (Compound 2b)

6-(N-tert-butyloxycarbonyl-6-aminohexanoyl)-8-chloromethyl-3,6,7,8-tetrahydro-1-methylbenzo[1,2-b:4,3-b']dipyrrol-4-ol (1c, 150 mg, 0.33 mmol) was treated with 5 mL of 3M HCl in ethyl acetate. The reaction mixture was stirred for 15 min and then evaporated in vacuo to dryness. To a solution of the resulting amine hydrochloride 6-(6-aminohexanoyl)-8-chloromethyl-3,6,7,8-tetrahydro-1-methylbenzo[1,2-b:4,3-b']dipyrrol-4-ol (1d) in 3 mL of anhydrous DMF was added NaH (41 mg, 1.7 mmol) suspended in 1 mL of DMF. After stirring for 30 min, a solution of $\underline{N,N}$-diisopropylethylamine hydrochloride (150 mg, 1.1 mmol) in 0.5 mL of DMF was added to quench excess NaH. The reaction mixture containing 2-(6-aminohexanoyl)-1,2, 8,8a-tetrahydro-7-methylcyclo-propa[c]pyrrolo[3,2-e]indol-4(5H)-one (2a) was immediately used for the next step. Bromoacetic acid $\underline{N}$-hydroxysuccinimide ester (180 mg, 0.7 mmol) was added and the mixture was stirred for 3 hours. The solvent was removed in vacuo and the resulting mixture was separated by reverse phase HPLC (PRP-1, Hamilton Co, 7×300 mm) in a gradient of acetonitrile in water (30–100%). The title compound (2b) was obtained as a colorless solid, after removal of the solvent, in 15% yield (from 1c):

$^1$H NMR (CDCl$_3$) δ9.84 (s, 1H), 6.85 (s, 1H), 6.69 (br s, 1H), 4.15 (m, 1H), 4.06 (s, 2H), 4.00 (m, 1H), 3.34 ( m, 2H), 2.89 (m, 1H), 2.52 (m, 2H), 2.02 (s, 3H), 1.99 (m, 1H, overlapping with CH$_3$ signal), 1.74 (m, 2H), 1.57 (m, 2H), 1.40 (m, 2H), 1.2 (m, 1H).

ODN synthesis

The unmodified 30-mer target ODN of Sequence Id. No: 3 was prepared from 10 μmol of polymeric support (Pharmacia) on an OligoPilot DNA synthesizer (Pharmacia) using the protocol supplied by the manufacturer. Standard reagents for the -cyanoethyl phosphoramidite coupling chemistry were purchased from Glen Research. 5' and 3' thiophosphate modifications were introduced using a phosphorylating phosphoramidite in combination with a sulfurizing reagent (Glen Research).

Synthesis of CPI-ODN conjugates

To a solution of an ODN with a terminal phosphorothioate of (Sequence Id. No: 4 or Sequence Id. No: 5, 50 A$_{260}$ units, ~0.25 μmol) in 20 μL of water were added triethylamine (0.5 μL) and 2-(N-bromoacetyl-6-aminohexanoyl)-1,2,8,8a-tetrahydro-7-methylcyclopropa[c]pyrrolo[3,2-e]indol-4 (5H)-one(2b, 20 μL of a 33 mM solution in DMF, 0.66 μmol). After 2 hours, the solution was diluted with 0.8 mL of water and loaded onto a reverse phase HPLC column (PRP-1, 7×300 mm). The CPI-ODN conjugates (Sequence Id. No: 6 and Sequence Id. No: 7, were resolved in 50–60% yields as cleanly separated peaks using an acetonitrile gradient (0–30%, 50 mM triethylammonium acetate pH 8). DNA crosslinking reaction.

The 30-mer target ODNs of Sequence Id. No: 3 (complementary) and of Sequence Id No: 8 (non-complementary) was 5' end-labeled by using T4 polynucleotide kinase and [-$^{32}$P]ATP and purified by 8% denaturing PAGE. CPI-ODNs (Sequence Id. No: 6 and Sequence Id. No: 7, 10 μM) were incubated with the complementary (Sequence Id. No: 3) or non-complementary (Sequence Id No: 8) 30-mer target ODNs (2 μM) in 10 mM HEPES, pH 7.4 and 100 mM NaCl either at 25° C. for 90 min or at 37° C. for 30 min. Crosslinked products were detected by direct analysis of reaction aliquots in an 8% denaturing polyacrylamide gel. Alkylation sites were further converted into nicks with 5' and 3' phosphate termini by incubation at 95° C. for 30 min in the reaction buffer, followed by treatment with 10% piperidine substantially in accordance with the method of Sugiyama et al. (1994) Chem. Res. Toxicol., 7, 673–683. Sites of cleavage in the target 30-mer were mapped relative to G and G+A sequencing ladders substantially in accordance with the method of Maxam et al. (1977) Proc. Natl. Acad. Sci. USA, 74, 560–564.) in an 8% denaturing polyacrylamide gel. The percent of alkylation was determined by quantitative phosphorimage analysis (Bio-Rad) of the cleavage products.

What is claimed is:

1. A covalently linked oligonucleotide and crosslinking agent conjugate wherein the sequence of the oligonucleotide is complementary or substantially complementary to a target sequence in nucleic acid, the conjugate having the formula R-LINKER-[X—(P=O)(Y)]$_q$—ODN where q is an integer selected from 0 or 1;

the X—(P=O)(Y)— group is at the 3' or 5' end or at both ends of the ODN;

X is O or S;

Y is O$^-$, S$^-$ or CH$_3$;

ODN is an oligonucleotide of approximately 3 to 500 nucleotide units, wherein the sugar moiety attached to the heterocyclic bases of the nucleotides is independently selected from β 2-deoxyribofuranose, and β-2-OR'-ribofuranose where R' is C$_{1-5}$-alkyl or C$_{2-5}$-alkenyl, the internudeotide linkages may optionally and independently include phosphorothioate and methylphosphonate linkages, and the ODN may optionally include an intercalator group, reporter group, lipophilic group or a minor groove binder covalently attached to the ODN;

the LINKER is a divalent moiety forming a covalent linkage between the ODN and (X—(P=O)(Y))$_q$ groups, of approximately 2 to 30 atoms length, and R is a group selected from the formulas (i) and (ii)

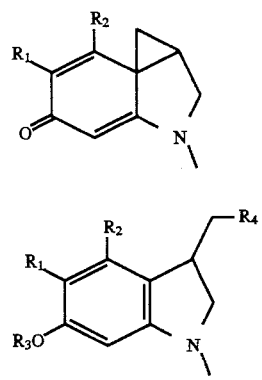

where R$_1$ and R$_2$ independently are H, alkyl of 1 to 6 carbons, alkoxy of 1 to 6 carbons, phenyl, (C$_{1-6}$alkyl) phenyl, heterocyclic consisting of a 5 to 7 membered ring and including 1 to 3 heteroatoms independently selected from the group consisting of O, N and S, (C$_{1-6}$alkyl)heterocyclic, or the R$_1$ and R$_2$ groups jointly form a carbocyclic ring of 5 to 7 atoms or a (C$_{1-6}$alkyl) carbocyclic ring of 5 to 7 atoms, a heterocyclic or a (C$_{1-6}$alkyl)heterocyclic ring where heterocyclic is defined as above, with the proviso that R$_1$ and R$_2$ are not both selected from the group consisting of phenyl, (C$_{1-6}$alkyl)phenyl, heterocyclic and (C$_{1-6}$alkyl) heterocyclic; R$_3$ is H or a group cleavable under physiological conditions;

R$_4$ is a leaving group, with the further proviso that when q is 0 then the LINKER group is attached to the 5 position of a uracil or to the 8 position of a purine base of a 5' or 3' terminal nucleotide of the ODN.

2. The oligonucleotide and crosslinking agent conjugate of claim 1 wherein the sugar moieties comprise β 2-deoxyribofuranose.

3. The oligonucleotide and crosslinking agent conjugate of claim 1 wherein the sugar moieties comprise β 2-O-methylribofuranose.

4. The oligonucleotide and crosslinking agent conjugate of claim 1 wherein q is 1.

5. The oligonucleotide and crosslinking agent conjugate of claim 1 wherein the R-LINKER-moiety is attached to the 3' end of the ODN.

6. The oligonucleotide and crosslinking agent conjugate of claim 1 wherein the R-LINKER-moiety is attached to the 5' end of the ODN.

7. The oligonucleotide and crosslinking agent conjugate of claim 1 wherein the ODN includes the sequences selected from the group consisting of 3'-TATAT and 3'-TTTTT.

8. The oligonucleotide and crosslinking agent conjugate of claim 1 wherein the R group is in accordance with formula (i).

9. The oligonucleotide and crosslinking agent conjugate of claim 1 wherein the R group is in accordance with formula (ii).

10. The oligonucleotide and crosslinking agent conjugate of claim 8 wherein the R$_1$ and R$_2$ groups jointly form a methylated pyrrol ring.

11. A covalently linked oligonucleotide and crosslinking agent conjugate wherein the sequence of the oligonucleotide is complementary or substantially complementary to a target sequence in nucleic acid, the conjugate having the formula

R-LINKER-X—(P=O)(Y)—ODN where the X—(P=O)(Y)— group is at the 3' or 5' end or at both ends of the ODN;

X is O or S;

Y is O$^-$, S$^-$ or CH$_3$;

ODN is an oligonucleotide of approximately 3 to 500 nucleotide units, wherein the sugar moiety attached to the heterocyclic bases of the nucleotides is independently selected from β 2-deoxyribofuranose, and β-2-OR'-ribofuranose where R' is C$_{1-5}$-alkyl or C$_{2-5}$-alkenyl, the internucleotide linkages may optionally and independently include phosphorothioate and methylphosphonate linkages, and the ODN may optionally include an intercalator group, reporter group, lipophilic group or a minor groove binder covalently attached to the ODN;

the LINKER is a divalent moiety forming a covalent linkage between the R and (X—(P=O)(Y))$_q$ groups, of approximately 2 to 30 atoms length, and R is a group selected from the formulas (i) and (ii)

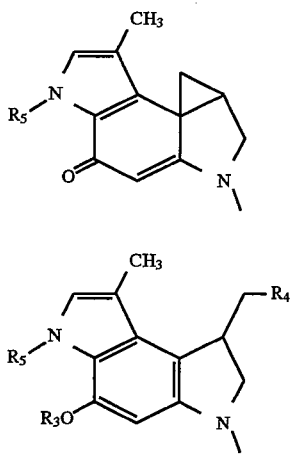

where
$R_3$ is H, alkanoyl having 1 to 6 carbons, phosphoryl or trimethylsilyl;
$R_4$ is a leaving group selected from the group consisting of Cl, Br, I and $OSO_2R''$ where R'' is $(C_{1-6})$alkyl, phenyl, tolyl, bromophenyl, nitrophenyl or trifluoromethyl, and
$R_5$ is H or alkyl of 1 to 6 carbons.

12. The oligonucleotide and crosslinking agent conjugate of claim 11 wherein the sugar moieties comprise β 2-deoxyribofuranose.

13. The oligonucleotide and crosslinking agent conjugate of claim 12 wherein $R_5$ is H or $CH_3$.

14. The oligonucleotide and crosslinking agent conjugate of claim 13 wherein the R group is in accordance with formula (i).

15. The oligonucleotide and crosslinking agent conjugate of claim 14 wherein the R-LINKER-moiety is attached to the 3' end of the ODN.

16. The oligonucleotide and crosslinking agent conjugate of claim 14 wherein the R-LINKER-moiety is attached to the 5' end of the ODN.

17. The oligonucleotide and crosslinking agent conjugate of claim 15 wherein the LINKER is selected from the groups consisting of:

—$O(CH_2)_mCO$—,

—$O(CH_2)_mNHCO$—,

—$O(CH_2)_mNHCO(CH_2)_nCO$—,

—$(CH_2)_mCO$—,

—$(CH_2)_mCONH(CH_2)_nCO$—,

—$(CH_2)_mCH(OH)(CH_2)_nNHCO(CH_2)_pNHCO$—,

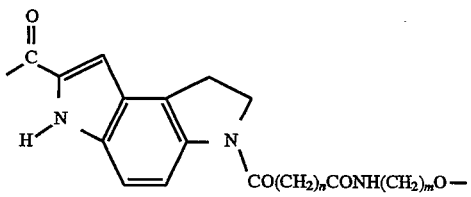

and

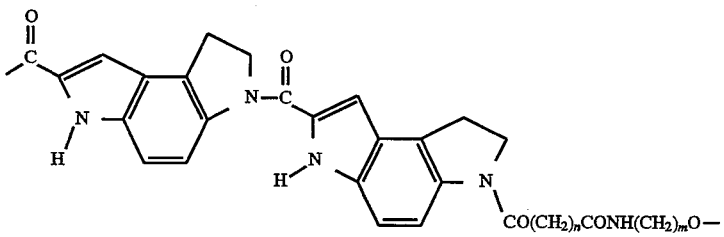

where m, n and p are integers having such a sum total that the R group is separated by no more than approximately 30 atoms from the ODN moiety.

18. The oligonucleotide and crosslinking agent conjugate of claim 17 wherein the LINER is selected from the groups consisting of:

—CO—$(CH_2)_n$—CONH—$(CH_2)_k$,

—CO—$(CH_2)_2$—CONH—$(CH_2)_2O(CH_2)_2$—,

—CO—$(CH_2)_{n''}$—$NHCOCH_2$—

—CO—$CH_2$—,

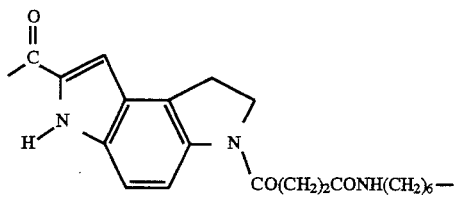

and

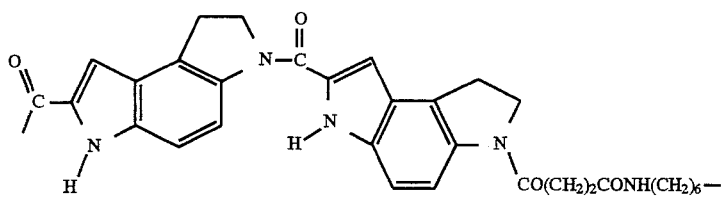

where n' is 2 or 3, k is 4 to 6 and n" is 2 to 5.

19. The oligonucleotide and crosslinking agent conjugate of claim 17 wherein the ODN includes the sequences selected from the group consisting of 3'-TATAT and 3'-TTTTT.

20. The oligonucleotide and crosslinking agent conjugate of claim 17 wherein X is S and the LINKER is —CO(CH$_2$)$_5$NHCOCH$_2$—.

21. A covalently linked oligonucleotide and crosslinking agent conjugate wherein the sequence of the oligonucleotide is complementary or substantially complementary to a target sequence in nucleic acid, the conjugate having the formula R-LINKER[X—(P=O)(Y)]$_q$—ODN where q is an integer selected from 0 or 1;

the X—(P=O)(Y)— group is at the 3' or 5' end or at both ends of the ODN;

X is O or S;

Y is O⁻, S⁻ or CH$_3$;

ODN is an oligonucleotide of approximately 3 to 500 nucleotide units, wherein the sugar moiety attached to the heterocyclic bases of the nucleotides is independently selected from β 2-deoxyribofuranose, and β-2-OR'-ribofuranose where R' is C$_{1-5}$-alkyl or C$_{2-5}$-alkenyl, the internucleotide linkages may optionally and independently include phosphorothioate and methylphosphonate linkages, and the ODN may optionally include an intercalator group, reporter group, lipophilic group or a minor groove binder covalently attached to the ODN;

the LINKER is a divalent moiety forming a covalent linkage between the ODN and (X—(P=O)(Y))$_q$ groups, of approximately 2 to 30 atoms length, and R is a group selected from the formulas (i) and (ii)

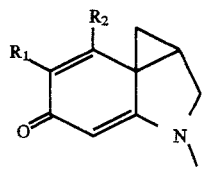

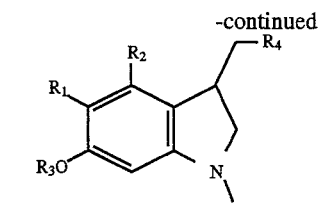

where R$_1$ and R$_2$ independently are H, alkyl of 1 to 6 carbons, alkoxy of 1 to 6 carbons, phenyl, (C$_{1-6}$alkyl)phenyl, heterocyclic consisting of a 5 membered ring and including one N as the heteroatom, (C$_{1-6}$alkyl)heterocyclic where heterocyclic is defined as above, or the R$_1$ and R$_2$ groups jointly form a carbocyclic ring of 5 to 7 atoms, or a (C$_{1-6}$alkyl)carbocyclic ring of 5 to 7 atoms, a heterocyclic or a (C$_{1-6}$alkyl)heterocyclic ring where heterocyclic is defined as above, with the proviso that R$_1$ and R$_2$ are not both selected from the group consisting of phenyl, (C$_{1-6}$alkyl)phenyl, heterocyclic and (C$_{1-6}$alkyl)heterocyclic;

R$_3$ is H, an alkanoyl group of 1 to 6 carbons, phosphoryl, or trialkylsilyl;

R$_4$ is Cl, Br, I, OSO$_2$R" where R" is (C$_{1-6}$)alkyl, phenyl, tolyl, bromophenyl, nitrophenyl or trifluoromethyl, with the further proviso that when q is 0 then the LINKER group is attached to the 5 position of a uracil or to the 8 position of a purine base of a 5' or 3' terminal nucleotide of the ODN.

22. The oligonucleotide and crosslinking agent conjugate of claim 21 where the R$_1$ and R$_2$ groups jointly form the heterocyclic or (C$_{1-6}$alkyl)heterocyclic ring.

23. The oligonucleotide and crosslinking agent conjugate of claim 21 where R$_3$ is H.

24. The oligonucleotide and crosslinking agent conjugate of claim 21 where R$_4$ is Cl.

25. The oligonucleotide and crosslinking agent conjugate of claim 21 where the R$_1$ and R$_2$ groups jointly form the heterocyclic or (C$_{1-6}$alkyl)heterocyclic ring, R$_3$ is H and R$_4$ is Cl.

* * * * *

UNITED STATES PATENT AND TRADEMARK OFFICE
CERTIFICATE OF CORRECTION

PATENT NO. : 5,659,022
DATED : August 19, 1997
INVENTOR(S) : Kutyavin et al.

It is certified that error appears in the above-indentified patent and that said Letters Patent is hereby corrected as shown below:

Column 2, line 28, "$NH_3$" should be --$NH_2$--.

Column 3, line 10, "$NH_3$" should be --$NH_2$--.

Column 5, line 39, "thy mine" should be --thymine--.

Column 7, line 22, "jointiy" should be --jointly--.

Column 9, line 14, "g" should be --q--.

Column 9, line 42, after "analog", delete ".".

Column 15, line 58, "$^1$HNMR" should be --$^1$H NMR--.

Column 15, line 61, "(chloro methyl)" should be --(chloromethyl)--.

Column 21, line 21, "internudeotide" should be --internucleotide--.

Column 24, line 58, after "-CO-$(CH_2)_n$, -CONH-$(CH_2)_k$", add -- - --.

Column 25, line 34, after "R-LINKER", add -- - --.

Column 26, line 52, "oligonudeotide" should be --oligonucleotide--.

Column 26, line 55, "oligonudeotide" should be --oligonucleotide--.

UNITED STATES PATENT AND TRADEMARK OFFICE
CERTIFICATE OF CORRECTION

PATENT NO. : 5,659,022
DATED : August 19, 1997
INVENTOR(S) : Kutyavin et al.

It is certified that error appears in the above-indentified patent and that said Letters Patent is hereby corrected as shown below:

Column 2, line 16, "therepeutic" should be --therapeutic--.
Column 6, line 58, "cylopropane" should be --cyclopropane--.
Column 7, lines 51-52, "neverthless" should be --nevertheless--.
Column 8, line 45, "ODB-CPI" should be --ODN-CPI--.
Column 13, line 3, "1d" should be --Id--.
Column 13, line 12, "1d" should be --Id--.
Column 15, line 15, after "agent)", add --.--.
Column 15, line 21, "cylopryl" should be --cyclopropyl--.

Signed and Sealed this

Sixth Day of January, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,659,022
DATED : August 19, 1997
INVENTOR(S) : Kutyavin et al.

It is certified that error appears in the above-indentified patent and that said Letters Patent is hereby corrected as shown below:

Column 21, line 29, "ODN"
should be --R--.

Signed and Sealed this

Twenty-fifth Day of August, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:1:

GGAGCTAACC GCTTTTTT                18

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:2:

TTTTTGCAC AACATGGG                18

( 2 ) INFORMATION FOR SEQ ID NO:3:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:3:

CCCATGTTGT GCAAAAAAGC GGTTAGCTCC                30

( 2 ) INFORMATION FOR SEQ ID NO:4:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i x ) FEATURE:
( A ) NAME/KEY: misc_binding
( B ) LOCATION: 18

( D ) OTHER INFORMATION: /bound_moiety= "phosphorothioate"

( x i ) SEQUENCE DESCRIPTION: SEQ ID NO:4:

GGAGCTAACC GCTTTTTT                                                                                          18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_binding
        ( B ) LOCATION: 1
        ( D ) OTHER INFORMATION: /bound_moiety= "phosphorothioate"

( x i ) SEQUENCE DESCRIPTION: SEQ ID NO:5:

TTTTTGCAC AACATGGG                                                                                            18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_binding
        ( B ) LOCATION: 18
        ( D ) OTHER INFORMATION: /bound_moiety= "phosphorothioate"
            / note= "attached to the sulphur is a moiety called
            2-(acetyl-6- aminohexanoyl)-1,2,8,8a-tetrahydro-7-
            methylcyclopropa[c]pyrrolo[3,2-e]indol-4(5H)-one"

( x i ) SEQUENCE DESCRIPTION: SEQ ID NO:6:

GGAGCTAACC GCTTTTTT                                                                                          18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_binding
        ( B ) LOCATION: 1
        ( D ) OTHER INFORMATION: /bound_moiety= "phosphorothioate"
            / note= "attached to the sulphur is a moiety called
            2-(acetyl-6- aminohexanoyl)-1,2,8,8a-tetrahydro-7-
            methylcyclopropa[c]pyrrolo[3,2-e]indol-4(5H)-one"

( x i ) SEQUENCE DESCRIPTION: SEQ ID NO:7:

TTTTTGCAC AACATGGG                                                                                            18

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCGTTGTCAG AAGTAAGTTG GGCCGCAGTG T                                                                            31